US012582289B2

(12) United States Patent
Miri et al.

(10) Patent No.: US 12,582,289 B2
(45) Date of Patent: Mar. 24, 2026

(54) ENHANCED VISION IN ELECTROSURGERY

(71) Applicant: Medtronic Advanced Energy LLC, Minneapolis, MN (US)

(72) Inventors: Mohammad Miri, Longmont, CO (US); Prakash Manley, Arvada, CO (US); Christopher T. Brown, Boulder, CO (US); Anjali Dhiman, Commerce City, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1253 days.

(21) Appl. No.: 17/198,630

(22) Filed: Mar. 11, 2021

(65) Prior Publication Data

US 2022/0287545 A1     Sep. 15, 2022

(51) Int. Cl.
| | |
|---|---|
| *A61B 1/00* | (2006.01) |
| *A61B 1/07* | (2006.01) |
| *A61B 18/00* | (2006.01) |
| *A61B 90/30* | (2016.01) |
| *H04N 5/262* | (2006.01) |
| *H04N 23/52* | (2023.01) |
| *H04N 23/698* | (2023.01) |

(52) U.S. Cl.
CPC ............. *A61B 1/0005* (2013.01); *A61B 1/07* (2013.01); *A61B 90/30* (2016.02); *H04N 5/2624* (2013.01); *H04N 5/2628* (2013.01); *H04N 23/52* (2023.01); *H04N 23/698* (2023.01); *A61B 2018/00982* (2013.01)

(58) Field of Classification Search
None
See application file for complete search history.

(56) References Cited

U.S. PATENT DOCUMENTS

| | | | |
|---|---|---|---|
| 5,015,243 A | | 5/1991 | Schifano |
| 5,409,484 A | | 4/1995 | Erlich et al. |
| 5,431,650 A | | 7/1995 | Cosmescu et al. |
| 5,451,223 A | | 9/1995 | Ben-Simhon |
| 5,667,478 A | * | 9/1997 | McFarlin ............... A61B 17/29 |
| | | | 600/101 |
| 5,830,214 A | | 11/1998 | Flom et al. |
| 5,836,944 A | | 11/1998 | Cosmescu |
| 7,357,802 B2 | | 4/2008 | Palanker et al. |
| 7,736,361 B2 | | 6/2010 | Palanker et al. |

(Continued)

OTHER PUBLICATIONS

Kim et al., "Designing a New Endoscope for Panoramic-View with Focus-Area 3D-Vision in Minimally Invasive Surgery", Journal of Medical and Biological Engineering, vol. 40, Apr. 2020, pp. 204-219.

(Continued)

*Primary Examiner* — Joanne M Rodden
*Assistant Examiner* — Nora W Rhodes
(74) *Attorney, Agent, or Firm* — Husch Blackwell LLP

(57) ABSTRACT
An electrosurgical device vision system, comprising at least one of one or more fiber-optic cables and/or digital image sensor positioned to capture a corresponding one or more views of the surgical site in proximity to a distal tip portion of an electrosurgical device, and a processor configured to utilize multiple images captured by the vision system to construct a composite image with at least one of an improved resolution, clarity, dynamic range, and/or size.

9 Claims, 7 Drawing Sheets

(56) References Cited

U.S. PATENT DOCUMENTS

| | | | |
|---|---|---|---|
| 8,457,461 | B2 | 6/2013 | Ott |
| 2005/0090816 | A1 | 4/2005 | McClurken et al. |
| 2009/0131932 | A1 | 5/2009 | Vakharia et al. |
| 2009/0258590 | A1 | 10/2009 | Prokash |
| 2011/0178515 | A1 | 7/2011 | Bloom et al. |
| 2012/0004657 | A1 | 1/2012 | Conley et al. |
| 2012/0016221 | A1 * | 1/2012 | Saadat ............. A61B 1/000094 |
| | | | 600/407 |
| 2012/0150101 | A1 | 6/2012 | Stearns et al. |
| 2013/0006260 | A1 | 1/2013 | Nakajima et al. |
| 2013/0110108 | A1 | 5/2013 | Davison et al. |
| 2013/0317352 | A1 * | 11/2013 | Case ..................... A61B 90/04 |
| | | | 382/128 |
| 2014/0100557 | A1 | 4/2014 | Bohner et al. |
| 2015/0112323 | A1 | 4/2015 | Hagg |
| 2016/0157920 | A1 | 6/2016 | Vayser et al. |
| 2018/0271581 | A1 | 9/2018 | OuYang et al. |
| 2019/0021782 | A1 | 1/2019 | Segit et al. |
| 2019/0387145 | A1 * | 12/2019 | Momiuchi ............. G03B 17/02 |
| 2020/0077974 | A1 * | 3/2020 | Avanaki ................. A61B 8/085 |
| 2021/0282654 | A1 * | 9/2021 | Cha ........................ A61B 1/046 |

OTHER PUBLICATIONS

Kim et al., "Performance Improvement for Two-Lens Panoramic Endoscopic System during Minimally Invasive Surgery", Journal of Healthcare Engineering, vol. 2019, Article ID 2097284, Nov. 19, 2019, 11 pages.
Kim et al., "Large-Field-of-View Visualization Utilizing Multiple Miniaturized Cameras for Laparoscopic Surgery", Micromachines, vol. 9, No. 9, 431, Aug. 25, 2018, 13 pages.
Written Opinion and International Search Report for PCT/US2018/043009 mailed Nov. 21, 2018.
International Preliminary Report on Patentability for PCT/US2018/043009 mailed Jan. 30, 2020.

* cited by examiner (Detail A)

ENHANCED VISION IN ELECTROSURGERY

TECHNICAL FIELD

The present technology is generally related to the field of medical devices, systems and methods for use upon a human body during surgery, and more particularly the present technology relates to vision systems and methods for electrosurgical devices.

BACKGROUND

Electrosurgery is a well-known technology that uses an applied electrical current to cut, oblate, or coagulate biological tissue. Electrosurgical devices enable surgeons to cut or otherwise remove tissue while at the same time providing bleeding control (coagulation), or to perform only coagulation without removing tissue. Electrosurgical devices function by applying an electrical potential (e.g., voltage) difference to the operative field where the tissue is to be treated between a pair of electrodes (generally one of which is positioned at the tip of the electrosurgical device). The operating principle is based on the formation of a thin layer of plasma or other heat source in proximity to the tip of the electrosurgical device. Typically some sort of conductive liquid medium (e.g., saline solution or bodily fluids surrounding the tip of the electrosurgical device) is vaporized to produce an ionized gas creating a thin layer of plasma surrounding the cutting portion of the electrosurgical device. The plasma, which is electrically conductive, effectively transfers the electrical potential to the tissue to be treated.

Transfer of the electrical potential via plasma enables a more controlled vaporization of the tissue targeted to be cut or ablated, while minimizing vaporization and thermal injury to the tissue surrounding the target tissue. The electrical potential can be applied as either a continuous train of high-frequency pulses or a continuous sinewave, often in the radio frequency range (e.g., having a pulse duration or wavelength in the range of between about 10 μs and about 10 ms). In some cases, the peak power of the pulses can be varied from pulse to pulse.

Although there are a variety of devices in existence, electrosurgical/electrocautery devices can generally be divided into two categories: devices having a bipolar arrangement and devices having a monopolar arrangement. In a bipolar arrangement, the electrical energy is applied between two electrodes arranged in close proximity to one another, generally in proximity to the tip of the electrosurgical device. One example of a bipolar arrangement device is the AQUAMANTYS Bipolar Sealer (manufactured by Medtronic). In a monopolar arrangement, the electrical energy is applied between a cutting electrode and a return electrode connected to the patient using a large surface return pad. One example of a monopolar arrangement device is the PLASMABLADE (manufactured by Medtronic).

The ability to control bleeding through the use of electrosurgical devices has led to advances in modern surgical techniques, including improvements in laparoscopic surgery. Laparoscopic surgery (sometimes referred to as "minimally invasive surgery"), is a technique in which an internal procedure (e.g., cholecystectomy, colectomy, nephrectomy, etc.) is performed through one or more small incisions made in the skin of the patient. Unfortunately, obtaining adequate views of the internal operative site continues to present limitations to modern laparoscopic surgical techniques.

Typically, a laparoscope (or other modified endoscope) is inserted through an incision in the patient's skin in order to provide the surgeon views of the operative site. For some types of surgical procedures, the surgeon may be able to insert the laparoscope and electrosurgical device through the same incision; however, more often separate incisions are required for the laparoscope and other surgical instruments. In surgical procedures were only a single incision is possible (e.g., discectomy, etc.), the surgeon must remove the electrosurgical device in order to insert the laparoscope. In these types of procedures, surgeons often rely on tactile feedback from the surgical tools as a guide during the procedure, rather than a view of the operative site through a laparoscope. The present disclosure addresses this concern.

SUMMARY OF THE DISCLOSURE

The techniques of this disclosure generally relate to an electrosurgical device including an integrated vision system configured to provide visualization of an operative surgical field, without the use of a separate laparoscope. In some embodiments, the enhanced electrosurgical vision systems and methods can employ a plurality of flexible fiber-optic cables running the length of the electrosurgical device to provide a moisture resistant, electromagnetic shielded, wide-angle panoramic digital display of the operative surgical field in real-time, through a single incision while the electrosurgical device is in use. In some embodiments, the enhanced electrosurgical vision systems and methods can employ a chip on a tip endoscope (or similar instrument) configured to provide real-time views of the surgical site.

One embodiment of the present disclosure provides an electrosurgical device, comprising an optical instrument configured to be coupled operably to an electrosurgical device, the optical instrument comprising at least one of a fiber-optic cable or digital image sensor positioned to capture a corresponding one or more source images of the surgical site in proximity to a distal tip portion of the electrosurgical device, and a processor configured to apply one or more homography matrices to combine the one or more source images into a composite image.

One embodiment of the present disclosure provides an electrosurgical device, comprising an optical instrument configured to be coupled operably to an electrosurgical device, the optical instrument comprising at least one of a fiber-optic cable or digital image sensor positioned to capture a corresponding one or more source images of the surgical site in proximity to a distal tip portion of the electrosurgical device, and a storage device comprising instructions that, when executed by a processor, apply one or more homography matrices to combine the one or more source images into a composite image.

One embodiment of the present disclosure provides an electrosurgical device, including an elongated body comprising a proximal handle portion, a distal tip portion, and a shaft portion located between the proximal handle portion and the distal tip portion, the distal tip portion configured to apply an electrical potential to biological tissue within a surgical site, so as to at least one of cut, oblate, or coagulate the biological tissue. The electrosurgical device further includes an optical instrument operably coupled to the shaft portion, the optical instrument comprising at least one of one or more fiber-optic cables and/or digital image sensors positioned to capture a corresponding one or more views of the surgical site in proximity to the distal tip portion, and a display configured to display the one or more views of the surgical site captured by the one or more fiber-optic cables.

In one embodiment, the one or more respective ends of the one or more fiber-optic cables are positioned at an angle of between about 5° and about 45° away from one another, so as to capture a wider field of view of the surgical site. In one embodiment, the each fiber-optic cable of the one or more fiber-optic cables has an outer diameter of between about 0.1-2.0 mm. In one embodiment, the electrosurgical device further includes one or more image sensors configured to convert the one or more views of the surgical site captured by the one or more fiber-optic cables to respective digital signals. In one embodiment, the one or more image sensors are configured to utilize at least one of an 8-bit, 10-bit, 12-bit, 16-bit, or 32-bit color depth. In one embodiment, the digital signals are sent to a processor for further processing. In one embodiment, the one or more views of the surgical site captured by the fiber-optic cables include wavelengths of light falling outside of the visible light range as an aid in obtaining views of biological tissue otherwise obscured by smoke or vaporized tissue. In one embodiment, the one or more views of the surgical site captured by the one or more fiber optic cables are stitched together to create a single larger view of the surgical site. In one embodiment, the electrosurgical device is configured to illuminate the surgical site by transmission of light through the one or more fiber-optic cables.

Another embodiment of the present disclosure provides an electrosurgical system, including a handheld electrosurgical instrument comprising a proximal handle portion, a distal tip portion, and a shaft portion located between the proximal handle portion and the distal tip portion, the distal tip portion configured to apply an electrical potential to biological tissue within a surgical site, so as to at least one of cut, oblate, or coagulate the biological tissue, an enhanced vision assembly operably coupled to the shaft portion, the enhanced vision assembly comprising at least one optical instrument positioned to capture a corresponding one or more views of the surgical site in proximity to the distal tip portion, and a control assembly operably coupled to the elongated body and the enhanced vision assembly via a cable assembly, the control assembly comprising a display configured to display the one or more views of the surgical site captured by the at least one optical instrument.

In one embodiment, the handheld electrosurgical instrument includes one or more pneumatic suction ports configured to evacuate smoke from the surgical site. In one embodiment, the at least one optical instrument is a camera. In one embodiment, the at least one optical instrument is housed in an electromagnetic shield to protect its signal from being distorted from the outside noise.

In one embodiment, the at least one optical instrument is housed in a waterproof shield protected from moisture intrusion. In one embodiment, the at least one optical instrument is one or more fiber-optic cables. In one embodiment, the cable assembly includes a fiber-optic connection between the control assembly and the enhanced vision assembly. In one embodiment, one or more respective ends of the one or more fiber-optic cables are positioned at an angle of between about 5° and about 45° away from one another, so as to capture a wider field of view of the surgical site. In one embodiment, the electrosurgical system further includes one or more image sensors configured to convert the one or more views of the surgical site captured by the one or more fiber-optic cables to respective digital signals. In one embodiment, the one or more views of the surgical site captured by the one or more fiber optic cables are stitched together to create a single larger view of the surgical site. In one embodiment, the electrosurgical device is configured to illuminate the surgical site by transmission of light through the one or more fiber-optic cables.

Another embodiment of the present disclosure provides a method of compositing one or more images of a surgical site, comprising capturing two or more source images of a surgical site in proximity to a distal tip portion of an electrosurgical device via two or more optical instruments operably coupled to the electrosurgical device, modifying the two or more source images according to one or more homography matrix. The homography matrix is configured to provide at least one of a rotational transformation, dilation, or translation of at least one of the two or more source images relative to a base image. The method further comprises combining the modified two or more source images to create a composite image. In embodiments, the method may also include displaying the composite image created from the modified two or more source images.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

Figures 1A, 1B:
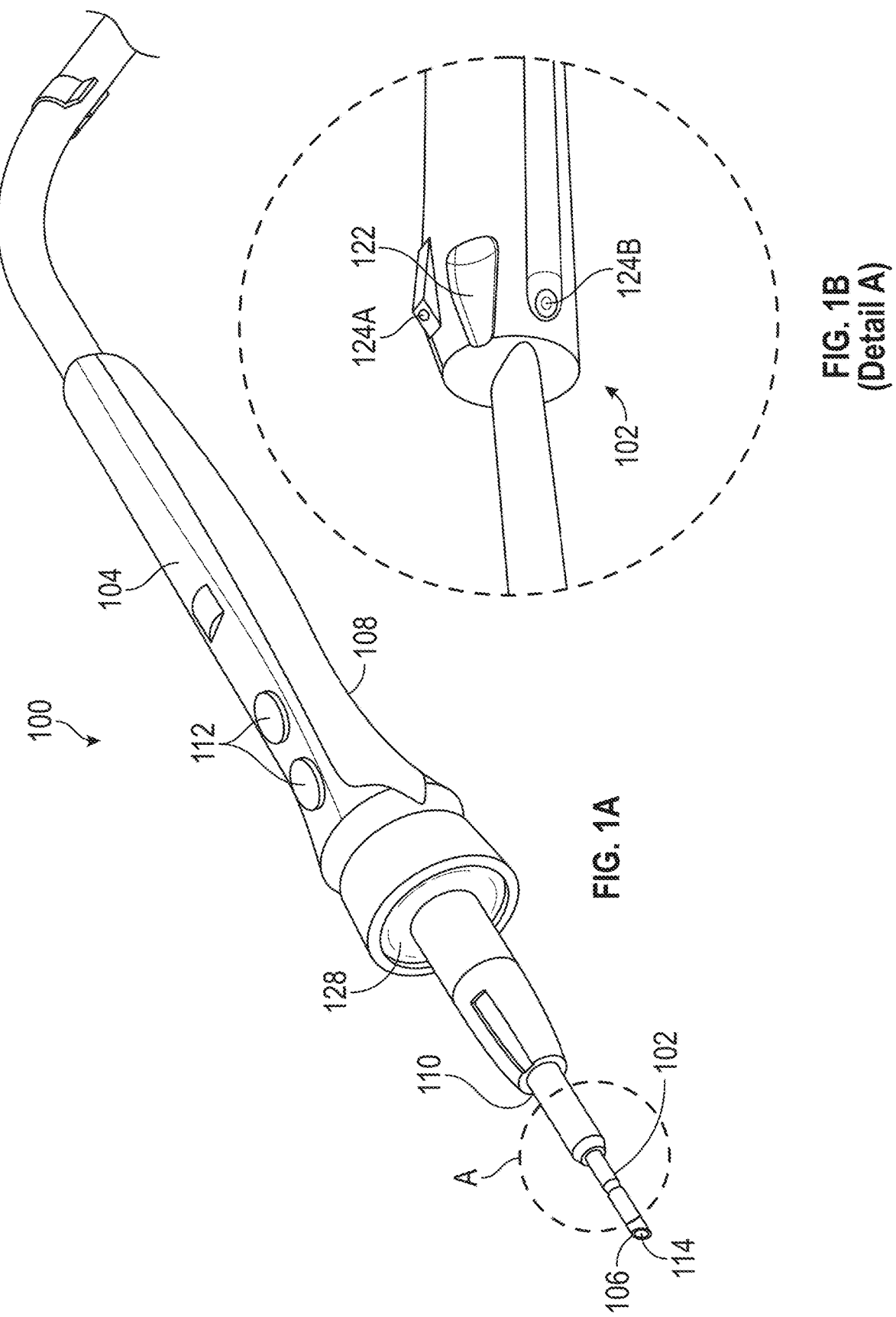
FIG. 1A is a perspective view depicting a handheld electrosurgical instrument, in accordance with an embodiment of the disclosure.
FIG. 1B is a close-up, perspective view depicting a distal portion of the handheld electrosurgical instrument of FIG. 1A, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1A, a handheld electrosurgical instrument 100 (alternatively referred to herein as an "electrosurgical device") configured to enable a real-time view of a surgical site during cutting, oblation or coagulation of biological tissue, is depicted in accordance with an embodiment of the disclosure. Accordingly, in some embodiments, the handheld electrosurgical device can include an enhanced vision assembly 102 configured to provide one or more views of the surgical site, without the need for separate laparoscope, endoscope, or the like. Moreover, embodiments of the present disclosure enable laparoscopic surgery previously requiring multiple incisions (e.g., a first incision for the electrosurgical device and a second incision for the laparoscope) to be performed with a single incision.

Figure 2:
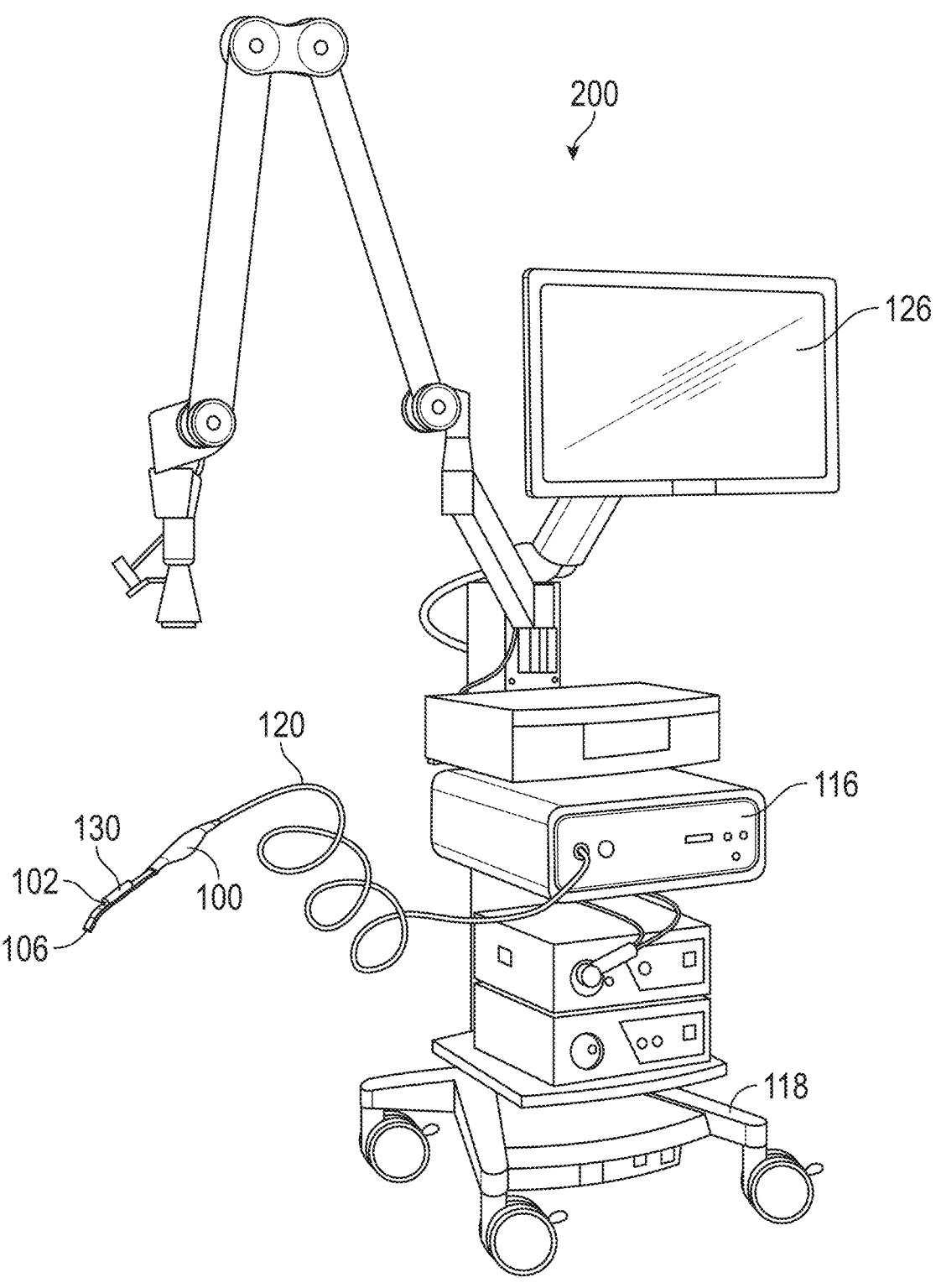
FIG. 2 is a perspective view of an electrosurgical system operably coupled to a wheeled cart, in accordance with an embodiment of the disclosure.

Although FIG. 1A depicts a monopolar arrangement device, other devices including bipolar arrangement devices (as depicted in FIG. 2) and other types of electrosurgical instruments are also contemplated. As such, the electrosurgical device 100 can be adapted for a variety of different procedures, including orthopedic procedures (e.g., knee, hip or shoulder arthroplasty, trauma procedures, etc.), spinal procedures (e.g., spinal fusion, laminotomy, discectomy, decompression, etc.), surgical oncology (e.g., hepatic recession, pancreatectomy, nephrectomy, etc.), cardiac implantable electronic device procedures (e.g., primary implants, generator replacement, upgrades, capsulectomies, etc.), neurosurgery procedures (e.g., open craniotomy, transsphenoidal procedures, etc.), thoracic procedures (e.g., lung resection, extrapleural pneumonectomy, chest wall resection, decortication, mediastinal lymphadenectomy, esophagectomy, etc.), and the like.

In some embodiments, the electrosurgical device 100 can include an elongated body 104, including a distal tip portion 106, a proximal handle portion 108, and a shaft portion 110 located between the distal tip portion 106 and the proximal end portion 108. The proximal hand portion 108 can include one or more control buttons 112, for example to electrically energized the distal tip portion 106, adjust the enhanced vision assembly 102, or the like. The distal tip portion 106 can include an insulated electrode 114 configured to enable the precise delivery of radiofrequency energy to the biological tissue of the surgical site. In some embodiments, distal tip portion 106 can be mounted on the shaft 110 (e.g., a telescoping shaft) enabling selective distal extension of the distal tip portion 106 relative to the proximal handle portion 108 to meet the needs of the surgical procedure. The various portions of the electrosurgical device 100 can be constructed of thermally insulated materials, and can have a nonstick coating for ease in cleaning during or after the procedure.

Figure 3:
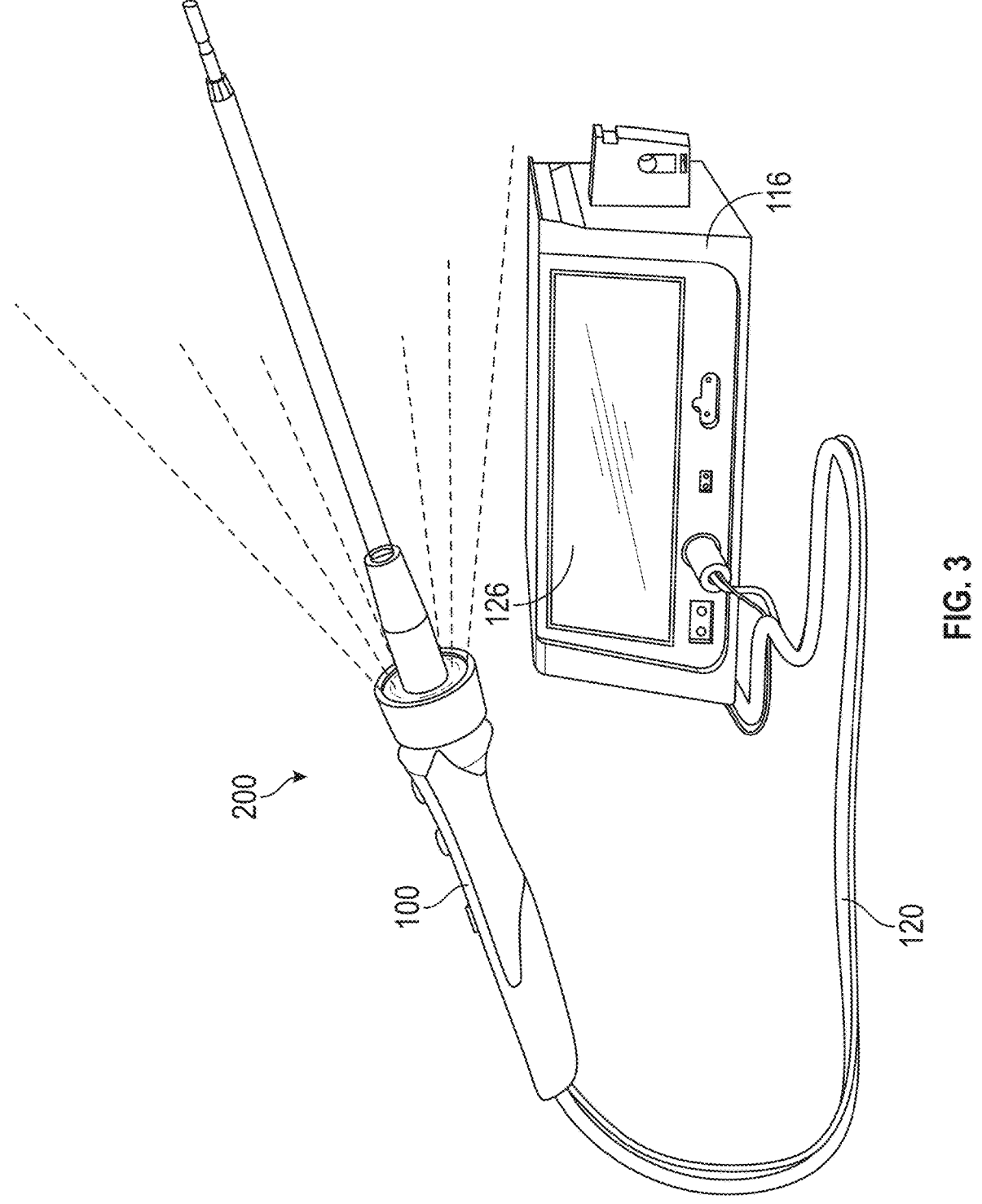
FIG. 3 is a perspective view of the mobile electrosurgical system, in accordance with an embodiment of the disclosure.

With additional reference to FIGS. 2 and 3, a electrosurgical system 200 configured to enable a real-time views of a surgical site without the use of a separate laparoscope, are depicted in accordance with embodiments of the disclosure. In some embodiments, a handheld electrosurgical device 100 can be operably coupled to a control assembly 116 configured to provide a consistent, reliable flow of energy to the device 100. For example, as depicted in FIG. 2, in some embodiments, the control assembly 116 can be mounted to a wheeled stand 118 for ease in movement within a surgical environment. In other embodiments, such as that depicted in FIG. 3, the control assembly 116 can be configured as a smaller, more portable device, potentially for use outside of a hospital or clinic setting.

In some embodiments, the electrosurgical system 200 can include a cable assembly 120, operably coupling the electrosurgical device to the control assembly 116, configured to provide an electrical, optical, and pneumatic connection between the control assembly 116 and the device 100. For example, in some embodiments, the cable assembly 120 can include one or more electrically conductive cables to provide radiofrequency energy to the distal tip portion 106, a pneumatic suction line (see e.g., pneumatic suction ports 122 of FIG. 1B) configured to evacuate smoke from the target site for improved visibility and safety, and one or more fiber-optic cables 124A/B (as depicted in FIG. 1B) configured to transmit images of the surgical site to the control assembly 116.

In some embodiments, the control assembly 116 can include a display 126 configured to display an image of the surgical site. In some embodiments, the control assembly 116 and display 126 can be configured to enable the capture of images (e.g., photography), video streaming, and recording of surgical procedures. In some embodiments, the electrosurgical device 100 can further be configured to provide illumination to the surgical site, for example via one or more LEDs 128 mounted in proximity to the handle portion 108 with a shaft portion 110, or by transmission of light through the one or more fiber-optic cables 124A/B. In some embodiments, the transmission of light to the surgical site via the one or more fiber-optic cables 124A/B, and the receipt of images from the surgical site via the one or more fiber-optic cables 124A/B can be performed simultaneously.

With continued reference to FIG. 2, in some embodiments, the enhanced vision assembly 102 can include an optical instrument in the form of camera 130 mounted in proximity to the distal tip 106 of the electrosurgical device 100 (e.g., operably coupled to the shaft portion 110). The camera 130 can be housed in an electromagnetic shield to protect its signal from being distorted from the outside noise (including the electromagnetic field generated by the electrosurgical device 100 itself). Further, the camera 130 can be housed in a waterproof shield protected from moisture intrusion during a surgical procedure. In some embodiments, the camera 130 can incorporate one or more optic lenses, an image sensor, signal conversion electronic circuitry, lights, and the like. In some embodiments the camera 130 located at the distal tip 106 of the device 100 may convert images to digital data without the use of a fiber optic cable. For example, in one embodiment, the camera 130 can be an endoscopic camera having an outer diameter of approximately 4 mm or less; although the use of other cameras for the enhanced vision system 102 are also contemplated.

Figure 4:
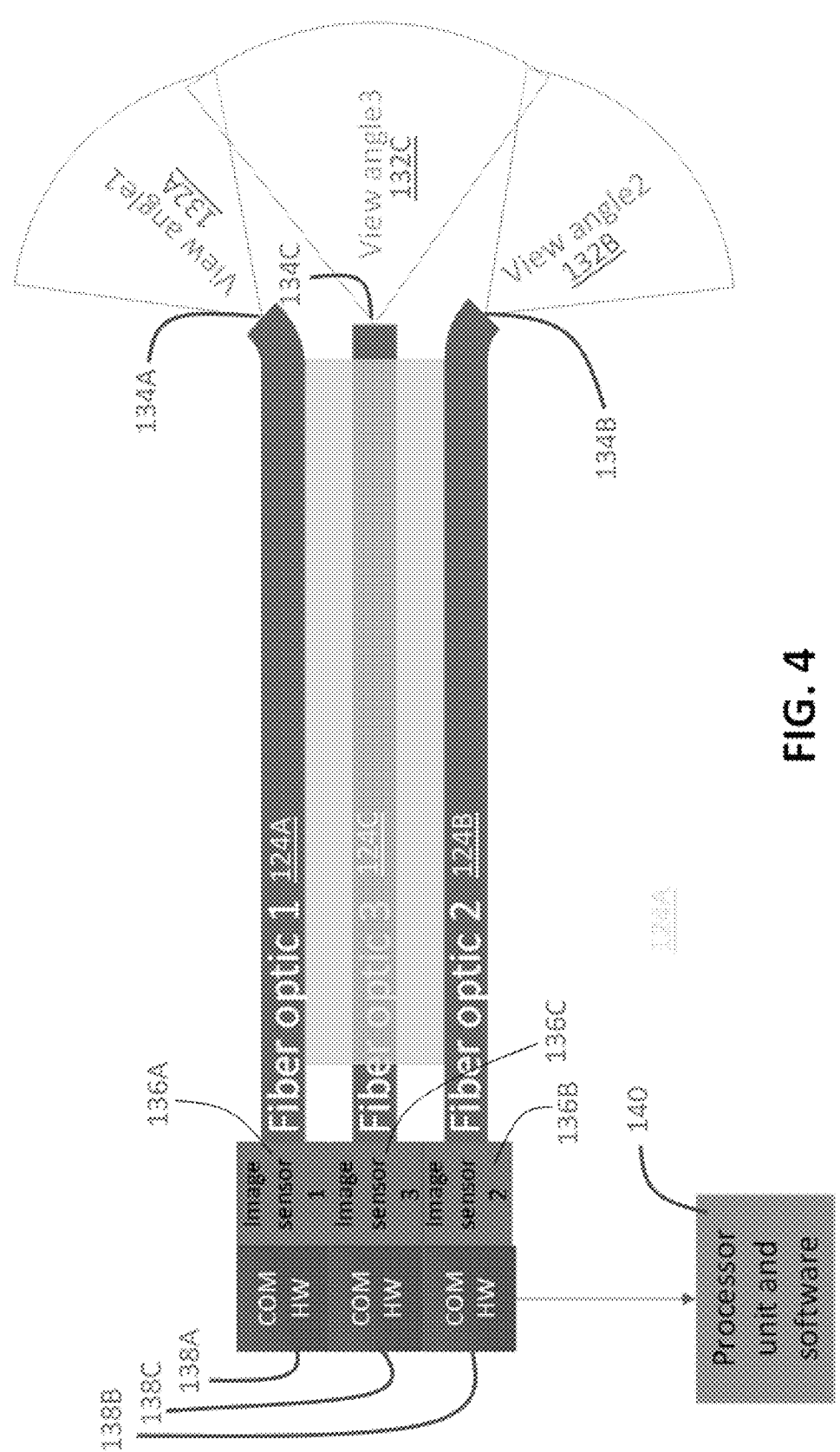
FIG. 4 is a schematic view depicting an enhanced vision assembly, in accordance with an embodiment of the disclosure.

Alternatively, as depicted in FIGS. 1A-B and 4, in some embodiments, the electrosurgical device 100 can include one or more fiber-optic cables 124A-C running axially along the shaft portion 110 of the electrosurgical device 100. In some embodiments, the one or more fiber-optic cables 124A-C can be positioned relative to the distal tip 106 of the electrosurgical device 100 in order to capture a wider range of views of the surgical site. For example, in some embodiments, the ends 134A-C of the one or more fiber optic cables 124A-C can be positioned in an angle of between about 5° and about 45° away from one another, so as to capture a wider field of view of the surgical site. In some embodiments, the view angles 132A-C of the respective one or more fiber optic cables 124A-C can be configured to provide overlapping views of discrete areas within the surgical pocket. Although the use of an electrosurgical device 100 including three fiber optic cables 124A-C is depicted, the use of a greater or lesser number of fiber optic cables is also contemplated. In some embodiments, each fiber-optic cable can have a diameter of between about 1.0-0.2 mm, such that collectively the shaft portion 110 of the device 100 (including the fiber-optic cables 124) measures between about 3-4 mm in diameter; although the use of other sizes of fiber-optic cable is also contemplated.

Images received by the one or more fiber optic cables 124A-C can be transmitted to one or more image sensors 136A-C. In some embodiments, each of the one or more fiber optic cables 124A-C can have its own dedicated digital image sensor, for example in the form of a Charge-Coupled Device (CCD) or other alternative image sensing arrangements. In other embodiments, the one or more fiber optic cables 124A-C can feed into a single image sensor. The one or more image sensors 136A-C can be operably coupled to one or more communication modules 138A-C for wired or wireless transmission of the digital signals received by the one or more sensors 136A-C to a processor unit 140 for further processing. In some embodiments, the processor 140 can be located within the control assembly 116. In other embodiments, the processor 140 can be a remotely located server, particularly where more complex machine learning or artificial intelligence algorithms may be employed in the processing of the captured images.

Although the removal of smoke and vaporized tissue can be affected by pneumatic suction (e.g. via one or more suction ports 122 as depicted in FIG. 1B), non-evacuated smoke and vaporized tissue can present an obstacle in obtaining a clear image of the surgical site. To obtain clearer images of the surgical site, in some embodiments, the one or more image sensors 136A-C can be configured to receive light outside of the visible spectrum (e.g., wavelengths outside of visible light range falling between about 380-780 nm). For example, in one embodiment, the one or more image sensors 136A-C can be configured to receive light with shorter wavelengths (ultraviolet) and/or longer wavelengths (infrared light) for conversion to visible images via the display 126. In one embodiment, the one or more image sensors 136A-C can be configured to receive light in the near infrared fluorescent range of between about 650-950 nm. In some embodiments, the imaging may be combined with other modalities, including but not limited to laser speckle imaging, thermal imaging, etc. In such embodiments, the ability of light falling outside of the normal visible spectrum to more easily penetrate smoke and vaporized tissue can provide better images of the surgical site. In such embodiments, a display of visible light gathered by the one or more image sensors 136A-C can be enhanced with converted nonvisible light (converted to a visible image) as an aid in obtaining a more comprehensive view of the surgical environment.

In some embodiments, the one or more image sensors 136A-C can be configured to capture light and color beyond the standard 8-bit color depth. The standard color depth makes use of an 8-bit per channel (RGB) system, combined to produce a 24-bit color representing one of 16,777,216 color variations ($2^{24}$). Although such systems produce more than the 10 million colors that the human eye can distinguish, processing systems including complex machine learning or artificial intelligence algorithms may benefit from more complex color schemes. Accordingly, in some embodiments, the one or more image sensors 136A-C can be configured to utilize more bits per channel (e.g. 8-bits, 10-bits, 12-bits, 16-bits, 32-bits, etc.), as an aid in providing a higher quality detail, particularly for use in further image processing. For example, in some embodiments, an image bit depth, including but not limited to 8-bits or higher, can be used for applications such as increased dynamic range, perfusion detection, lowlight imaging, spectrometry, etc. For example, in some embodiments, the processor unit 140 can be configured to aid in tissue detection by, for example, adding lines to distinguish between tissue types or artificially changing the color of certain types of tissue (e.g., highlighting the tissue to be ablated or cut). Other types of image processing are also contemplated.

Figure 5:
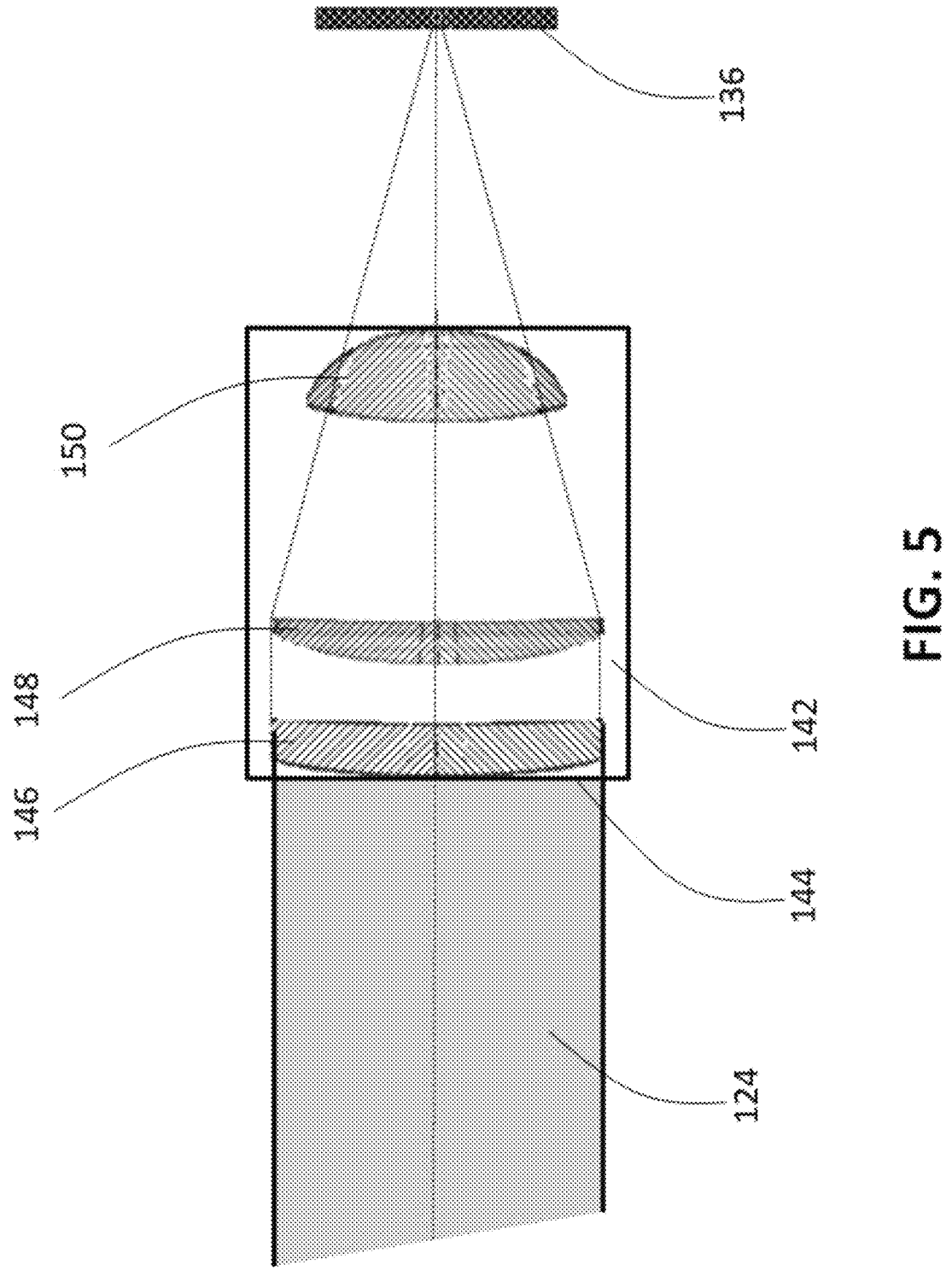
FIG. 5 is a schematic view depicting a fiber-optic cable, lens assembly, and image sensor, in accordance with an embodiment of the disclosure.

With reference to FIG. 5, a lens assembly 142 for the enhanced vision assembly 102 is depicted in accordance with an embodiment of the disclosure. In some embodiments, the lens assembly 142 can be configured as a macro lens assembly positioned at a proximal end 144 and/or distal end 134 of each fiber-optic cable 124, providing a dedicated lens that is adapted to capture sharp, high detailed images of the surgical site at with a short focal distance. For example, in some embodiments, the lens assembly 142 can be configured to provide a magnified view of the surgical site for improved visualization of the affected tissue. In one embodiment, the lens assembly 142 can include a first lens 146, a second lens 148, and a third lens 150 arrangement configured to focus images captured by the optic cable 124 onto the image sensor 136. In other embodiments, one or more of the lenses can be shaped into either a distal end 134 or proximal end 144 of the fiber optic cable 124 (e.g., via shaping of the end of the fiber-optic cable itself). For example, in one embodiment, a proximal end 144 of the fiber optic cable 124 can have either of a convex or concave surface.

Figures 6A, 6B, 6C, 7:
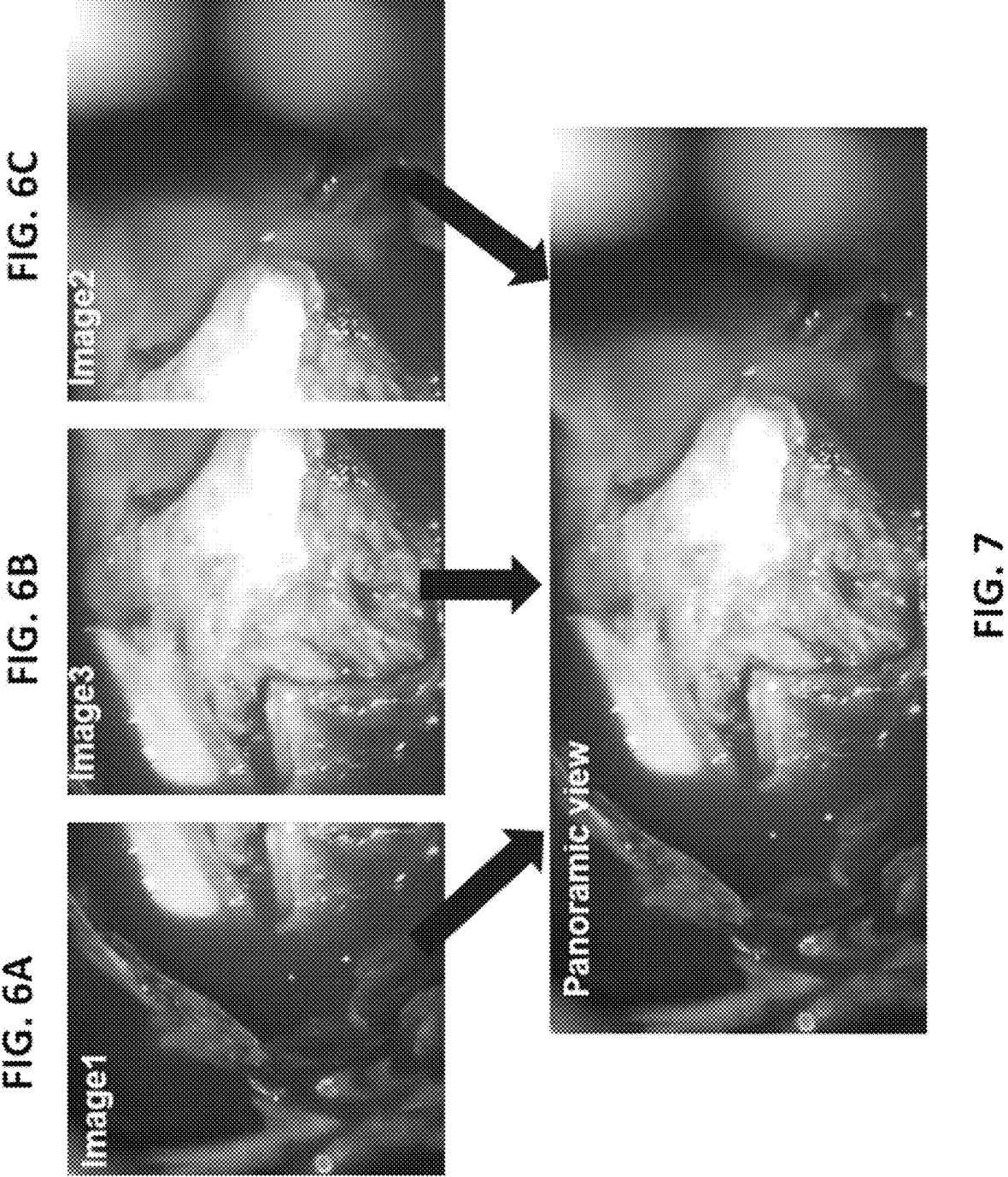
FIG. 6A-C represent views of a surgical site captured by corresponding optical instruments, in accordance with an embodiment of the disclosure.
FIG. 7 represents a single larger, panoramic view in which the views of FIGS. 6A-C have been stitched together, in accordance with an embodiment of the disclosure.

In yet another embodiment, the enhanced vision system 102 can utilize synthetic aperture imaging or other computational photography methods utilizing multiple images to construct an image with better resolution, clarity, dynamic range, size, etc. With reference to FIG. 6A-D, multiple images gathered by the various optic cables 124 (or cameras 130) can be combined to create a single, wide angle, panoramic view of the surgical site as an aid in obtaining better visualization of the surrounding area. For example, in some embodiments, a first image (as depicted in FIG. 6A), second image (as depicted in FIG. 6B) and third image (as depicted in FIG. 6C), respectively captured by fiber optic cables 124A-C can be digitally combined to form a panoramic view (as depicted in FIG. 7) for display on the display 126. In some embodiments, the stitching of the images together can be performed by the processor unit 140.

Figure 8:
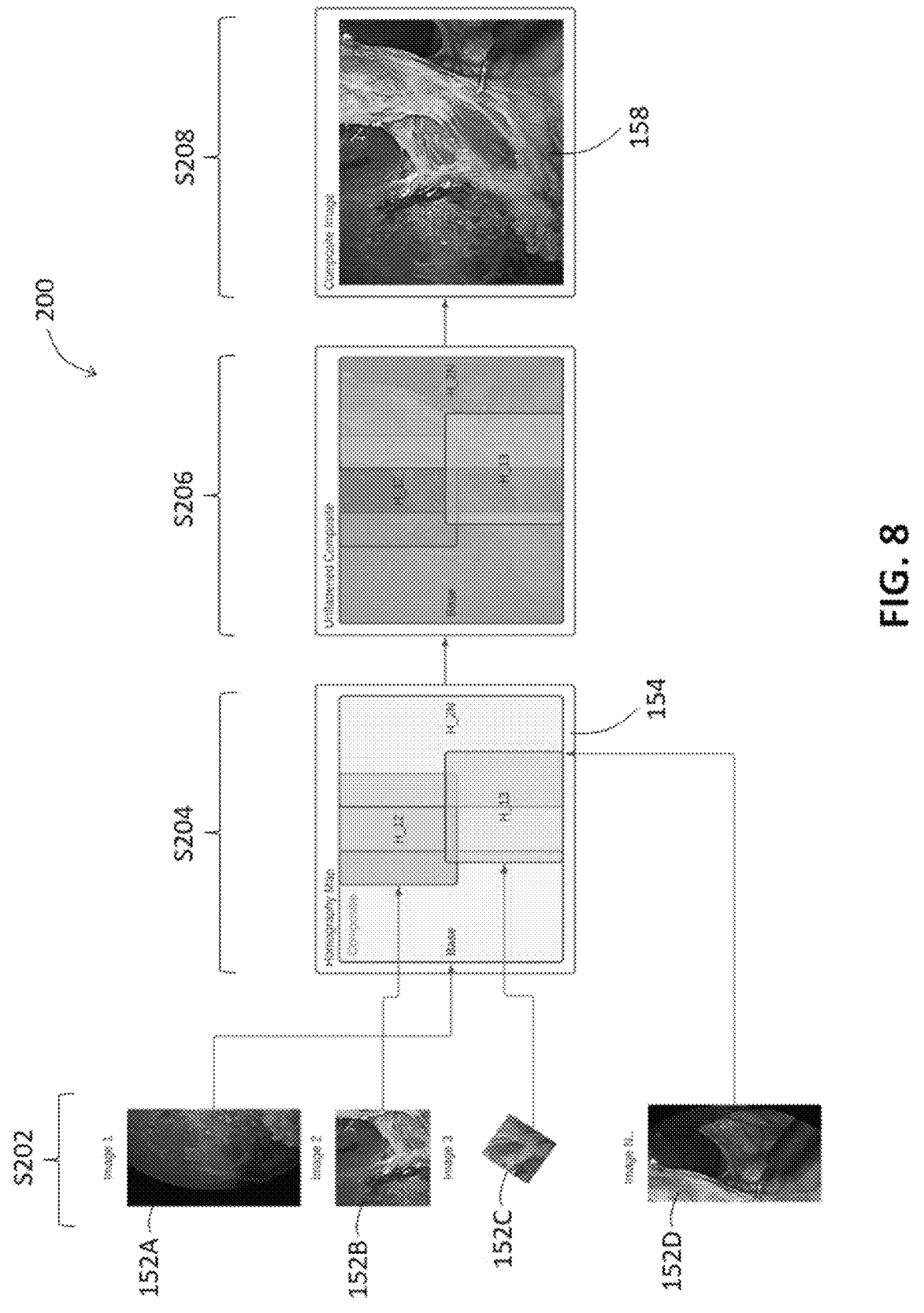
FIG. 8 is a flowchart depicting a method of compositing one or more images, in accordance with an embodiment of the disclosure.

Referring to FIG. 8, a flowchart depicting a method of compositing one or more images 200 is depicted in accordance with an embodiment of the disclosure. At S202, one or more individual source images 152A-D can be captured by a corresponding one or more image sensors. In some embodiments, individual source images 152A-D can be utilized directly without compositing for tasks including but not limited to disparity mapping for depth sensing, motion detection, object detection, perfusion detection, etc. Additional filters including but not limited to the warping transformations, color correction, lowlight correction, and obstruction removal can be applied to individual source images 152A-D prior to compositing. Algorithms for manipulation of the individual source images 152A-D can include traditional algorithms, machine learning algorithms or any combinations thereof.

At S204, multiple individual source images 152A-D can be related to one another through homography. For example, in some embodiments, a homography map 154 can be used to align the captured individual source images 152A-D with one another in the creation of a composite image 158. In some embodiments, homography map 154 can describe a set of linear algebra operations, which when applied to an individual source image (or set of individual source images) can geometrically transform the image to a desired shape and position, thereby enabling the image to be stitched together with other images to create the composite image 158.

For example, in some embodiments the homography map 154 can be composed of several homography matrices which describe the transformation of a source image (e.g., image 1, image 2, image 3, image N., etc.) into a modified image (e.g., base, H_12, H_13, H_2N, etc.), as depicted in FIG. 8. In the particular example depicted, the "base" image is taken to be "image 1," such that the homography matrices are computed in relation to the base image from left to right. As further depicted in this embodiment, "H_13" would be the homography matrix for "image 3," describing a rotational transformation, a dilation, and a translation relative to the origin of "image 1."

The homography map 154 can be generated by several methods, including K-means clustering of like points of high contrast within an image (e.g., traditional panorama), or an analytical solution can be derived based on image sensor properties and positioning (e.g., wherein image sensor configuration is known). The particular chosen "base" image and order of homography matrix computation is arbitrary; further, not all source images 152A-D may require all types of transformations. In some embodiments, the use of a precomputed homography map 154 is desired, as while the original computation of a homography map 154 is relatively computationally demanding, the use of a precomputed homography map 154 to automatically transform the source images into the modified images according to predefined criteria is computationally trivial and essentially independent of image resolution, thereby enabling the real-time creation of a live composite video.

At S206, the modified images of the homography map 154 are flattened into a single composite image. For example, in some embodiments, the modified images can be flattened by digital methods, such as bitwise addition, alpha blending, etc., thereby producing a completed composite image 158 at S208. In some embodiments, computational filters, including but not limited to, de-warping transformations, color correction, lowlight correction, and obstruction removal can be applied to the composite image 158. Utilized algorithms can include traditional algorithms, machine learning algorithms, or any combination thereof.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electrosurgical device, comprising:
an optical instrument configured to be coupled operably to the electrosurgical device and positioned to capture source images of the surgical site in proximity to a distal tip portion of the electrosurgical device, the optical instrument comprising:
a plurality of fiber-optic cables arranged axially along a length of the electrosurgical device, each configured to obtain separate source images, and wherein an end of at least one of the fiber-optic cables is positioned at an angle of between about 5° and about 45° away from a longitudinal axis of the electrosurgical device;
a digital image sensor coupled to the plurality of fiber-optic cables;
an electromagnetic shield configured to protect the optical instrument from distortion created by the electrosurgical device during operation; and
a storage device comprising instructions that, when executed by a processor, apply one or more homography matrices to combine the source images into a composite image depicting a wider field of view of the surgical site than possible from one of the plurality of fiber-optic cables.

2. The electrosurgical device of claim 1, wherein the optical instrument comprises a fiber-optic cable having an outer diameter of between about 0.1 mm and about 2.0 mm.

3. The electrosurgical device of claim 1, wherein the optical instrument comprises a digital image sensor configured to utilize at least one of an 8-bit, 10-bit, 12-bit, 16-bit, or 32-bit color depth.

4. The electrosurgical device of claim 1, wherein the one or more views of the surgical site captured by at least one of the fiber-optic cable or digital image sensor include wavelengths of light falling outside of the visible light range as an aid in obtaining views of biological tissue otherwise obscured by smoke or vaporized tissue.

5. The electrosurgical device of claim 1, wherein the electrosurgical device is configured to illuminate the surgical site by transmission of light through at least one of the fiber-optic cable or digital image sensor.

6. The electrosurgical device of claim 1, wherein the optical instrument further comprises an optical lens arranged at a proximal end or a distal end of the fiber-optic cable.

7. A method of compositing one or more images of a surgical site, comprising:
capturing source images of the surgical site in proximity to a distal tip portion of an electrosurgical device via two or more optical instruments operably coupled to the electrosurgical device, each of the optical instruments including a fiber-optic cable arranged axially along a length of the electrosurgical device for obtaining a separate source image of the surgical site, a digital image sensor to convert an obtained image to a digital signal, and an electromagnetic shield configured to protect the optical instrument from distortion created by the electrosurgical device during operation, wherein an end of at least one of the fiber-optic cables is positioned at an angle of between about 5° and about 45° away from a longitudinal axis of the electrosurgical device;

modifying the source images according to one or more homography matrix, wherein the homography matrix is configured to provide at least one of a rotational transformation, dilation, or translation of at least one of the two or more source images relative to a base image; and combining the modified two or more source images to create a composite image depicting a wider field of view of the surgical site than possible from one of the plurality of fiber-optic cables.

8. The method of claim 7, wherein the two or more source images include wavelengths of light falling outside of the visible light range as an aid in obtaining views of biological tissue otherwise obscured by smoke or vaporized tissue.

9. The method of claim 7, wherein the two or more source images have at least one of an 8-bit, 10-bit, 16-bit, or 32-bit color depth.

* * * * *